US006218573B1

(12) United States Patent
Vassiliou et al.

(10) Patent No.: US 6,218,573 B1
(45) Date of Patent: Apr. 17, 2001

(54) METHODS OF RECOVERING CATALYST IN SOLUTION IN THE OXIDATION OF CYCLOHEXANE TO ADIPIC ACID

(75) Inventors: Eustathios Vassiliou, Newark, DE (US); Mark W. Dassel, Indianola, WA (US); Ader M. Rostami; Douglas J. Dudgeon, both of Bainbridge Island, WA (US); David C. DeCoster, Buckley, WA (US)

(73) Assignee: RPC Inc., Atlanta, GA (US)

( * ) Notice: Subject to any disclaimer, the term of this patent is extended or adjusted under 35 U.S.C. 154(b) by 0 days.

(21) Appl. No.: 09/345,876

(22) Filed: Jun. 30, 1999

Related U.S. Application Data

(60) Provisional application No. 60/111,848, filed on Dec. 11, 1998, provisional application No. 60/110,206, filed on Nov. 30, 1998, provisional application No. 60/105,048, filed on Oct. 20, 1998, provisional application No. 60/093,256, filed on Jul. 17, 1998, and provisional application No. 60/091,483, filed on Jul. 2, 1998.

(51) Int. Cl.$^7$ ....................................................... C07L 51/31

(52) U.S. Cl. .............................................................. 562/543

(58) Field of Search ........................... 502/155; 528/322; 562/413, 410, 412, 411, 543

(56) References Cited

U.S. PATENT DOCUMENTS

| 1,121,532 | 12/1914 | Newberry . |
| 1,867,933 | 7/1932 | Wilton . |
| 2,014,044 | 9/1935 | Haswell . |
| 2,223,493 | 12/1940 | Loder . |
| 2,223,494 | 12/1940 | Loder et al. . |
| 2,301,240 | 11/1942 | Baumann et al. . |
| 2,439,513 | 4/1948 | Hamblet et al. . |
| 2,557,282 | 6/1951 | Hamblet et al. . |
| 2,565,087 | 8/1951 | Porter et al. . |
| 2,980,523 | 4/1961 | Dille et al. . |
| 3,161,603 | 12/1964 | Leyshon et al. . |
| 3,231,608 | 1/1966 | Kollar . |
| 3,234,271 | 2/1966 | Barker et al. . |
| 3,290,369 | 12/1966 | Bonfield et al. . |
| 3,361,806 | 1/1968 | Lidov . |
| 3,386,810 | 6/1968 | Burke, Jr. et al. . |
| 3,390,174 | 6/1968 | Schulz et al. . |
| 3,515,751 | 6/1970 | Oberster et al. . |
| 3,522,018 | 7/1970 | Bachmann et al. . |
| 3,530,185 | 9/1970 | Pugi . |
| 3,613,333 | 10/1971 | Gardenier . |
| 3,649,685 | 3/1972 | Ishimoto et al. . |
| 3,677,696 | 7/1972 | Bryk et al. . |
| 3,819,813 | 6/1974 | Jones, Jr. et al. . |
| 3,839,435 | 10/1974 | Shigeyasu et al. . |
| 3,869,508 | 3/1975 | Longley et al. . |
| 3,928,005 | 12/1975 | Laslo . |
| 3,932,513 | 1/1976 | Russell . |
| 3,946,076 | 3/1976 | Paasen et al. . |
| 3,957,876 | 5/1976 | Rapoport et al. . |
| 3,987,100 | 10/1976 | Barnette et al. . |
| 3,987,808 | 10/1976 | Carbonell et al. . |

(List continued on next page.)

FOREIGN PATENT DOCUMENTS

| 2 309 423 | 8/1974 | (DE) . |
| 4426132 A1 | 1/1996 | (DE) . |
| 4427474 A1 | 2/1996 | (DE) . |
| 1143213 | 2/1969 | (EP) . |
| 439 007 A2 | 7/1991 | (EP) . |
| 494 416 A2 | 7/1992 | (EP) . |
| 729 084 A1 | 8/1996 | (EP) . |
| 729 085 A1 | 8/1996 | (EP) . |
| 751 105 A2 | 1/1997 | (EP) . |
| 2 722 783 A1 | 1/1996 | (FR) . |
| 415172 | 8/1934 | (GB) . |
| 738808 | 10/1955 | (GB) . |
| 864106 | 3/1961 | (GB) . |
| 2 014 473 | 8/1979 | (GB) . |
| 2 072 667 | 10/1981 | (GB) . |
| 48-003815 | 2/1973 | (JP) . |
| 50-034006B | 11/1975 | (JP) . |
| 54-33891 | 3/1979 | (JP) . |
| 61 063634 | 4/1986 | (JP) . |
| WO 94/07833 | 4/1994 | (WO) . |
| WO 94/07834 | 4/1994 | (WO) . |
| WO 96/03365 | 2/1996 | (WO) . |
| WO 96/14288 | 5/1996 | (WO) . |
| WO 96/40610 | 12/1996 | (WO) . |
| WO 97/49485 | 12/1997 | (WO) . |

OTHER PUBLICATIONS

E. Sorribes et al., "Formación de nuevas fases en el proceso de obtención de ácido adípico: causas y efectos que provocan," *Rev. R. Acad. Cienc. Exactas, Fis. Nat. Madrid* (1987), 81 (1), 233–5 (+English language translation).

Lewis, *Hawley's Condensed Chemical Dictionary*, 12$^{th}$ ed., 1993, pp. 7, 336, and 1076.

*Primary Examiner*—Paul J. Killos
(74) *Attorney, Agent, or Firm*—Seed Intellectual Property Law Group PLLC

(57) ABSTRACT

This invention relates to methods of controlling the oxidation of cyclohexane to adipic acid in the presence of a monobasic acid solvent, by removing the catalyst from the reaction mixture, outside the reaction zone. Substantially all the unreacted cyclohexane along with at least the majority of the monobasic acid solvent are removed. A substantially non-solvent for the catalyst (first constituent), and water are added into the resulting mixture, in such amounts as to maintain one solids-free single liquid phase. This process is highly facilitated in the presence of considerable amounts of adipic acid. The catalyst may then be extracted with water from the solids-free single liquid phase. A water phase containing dissolved catalyst may also be formed by addition of small amounts of a solvent which is substantially non-solvent for the catalyst and substantially non-solvent for the dibasic acids (second constituent), and/or dropping the temperature. Adipic acid may be precipitated after catalyst removal with further addition of second constituent and/or dropping the temperature.

51 Claims, 2 Drawing Sheets

U.S. PATENT DOCUMENTS

| | | |
|---|---|---|
| 4,025,498 | 5/1977 | Buss et al. . |
| 4,032,569 | 6/1977 | Onopchenko et al. . |
| 4,039,304 | 8/1977 | Bechthold et al. . |
| 4,055,600 | 10/1977 | Langley et al. . |
| 4,065,527 | 12/1977 | Graber . |
| 4,158,739 | 6/1979 | Schulz et al. . |
| 4,160,108 | 7/1979 | Shigeyasu et al. . |
| 4,161,573 | 7/1979 | Gunsher et al. . |
| 4,200,617 | 4/1980 | Levy . |
| 4,263,453 | 4/1981 | Schulz et al. . |
| 4,269,805 | 5/1981 | Schoengen et al. . |
| 4,308,037 | 12/1981 | Meissner et al. . |
| 4,332,590 | 6/1982 | Smith . |
| 4,361,965 | 12/1982 | Goumondy et al. . |
| 4,370,304 | 1/1983 | Hendriks et al. . |
| 4,394,139 | 7/1983 | Board . |
| 4,419,184 | 12/1983 | Backlund . |
| 4,423,018 | 12/1983 | Lester, Jr. et al. . |
| 4,477,380 | 10/1984 | Knips et al. . |
| 4,543,399 | 9/1985 | Jenkins, III et al. . |
| 4,588,790 | 5/1986 | Jenkins, III et al. . |
| 4,603,220 | 7/1986 | Feld . |
| 4,902,827 | 2/1990 | Steinmetz et al. . |
| 4,989,452 | 2/1991 | Toon et al. . |
| 5,061,453 | 10/1991 | Krippl et al. . |
| 5,104,492 | 4/1992 | King et al. . |
| 5,117,007 | 5/1992 | Taheri . |
| 5,123,936 | 6/1992 | Stone et al. . |
| 5,139,753 | 8/1992 | Hardison . |
| 5,170,727 | 12/1992 | Nielsen . |
| 5,206,701 | 4/1993 | Taylor et al. . |
| 5,221,800 | 6/1993 | Park et al. . |
| 5,244,603 | 9/1993 | Davis . |
| 5,259,996 | 11/1993 | Morgan . |
| 5,270,019 | 12/1993 | Melton et al. . |
| 5,271,904 | 12/1993 | Esposito et al. . |
| 5,286,458 | 2/1994 | Yang et al. . |
| 5,294,378 | 3/1994 | Succi et al. . |
| 5,312,567 | 5/1994 | Kozma et al. . |
| 5,321,157 | 6/1994 | Kollar . |
| 5,374,767 | 12/1994 | Drinkard et al. . |
| 5,396,850 | 3/1995 | Conochie et al. . |
| 5,399,750 | 3/1995 | Brun et al. . |
| 5,463,119 * | 10/1995 | Kollar . |
| 5,502,245 | 3/1996 | Dassel et al. ............ 562/413 |
| 5,505,920 | 4/1996 | Kollar et al. ............ 423/246 |
| 5,516,423 | 5/1996 | Conoby et al. ............ 210/85 |
| 5,547,905 | 8/1996 | Kulsrestha et al. ............ 502/66 |
| 5,558,842 | 9/1996 | Vassiliou et al. ............ 422/108 |
| 5,580,531 | 12/1996 | Vassiliou et al. ............ 422/108 |
| 5,654,475 | 8/1997 | Vassiliou et al. ............ 562/413 |
| 5,756,837 | 5/1998 | Costantini et al. ............ 562/543 |
| 5,801,273 | 9/1998 | Vassiliou et al. ............ 562/413 |
| 5,801,282 | 9/1998 | Dassel et al. ............ 562/413 |
| 5,817,868 | 10/1998 | Rostami et al. ............ 562/413 |
| 5,824,819 | 10/1998 | Dassel et al. ............ 562/529 |
| 5,877,341 | 3/1999 | Vassiliou et al. ............ 560/77 |
| 5,883,292 | 3/1999 | Dassel et al. ............ 562/413 |
| 5,908,589 | 6/1999 | DeCoster et al. ............ 264/37.18 |
| 5,922,908 | 7/1999 | Dassel et al. ............ 562/543 |
| 5,929,277 | 7/1999 | DeCoster et al. ............ 562/593 |

* cited by examiner

METHODS OF RECOVERING CATALYST IN SOLUTION IN THE OXIDATION OF CYCLOHEXANE TO ADIPIC ACID

CROSS REFERENCE TO RELATED APPLICATIONS

This application claims priority from U.S. Provisional Applications No. 60/091,483, filed Jul. 2, 1998, No. 60/093,256, filed Jul. 17, 1998, No. 60/105,048, filed Oct. 20, 1998, No. 60/110,206, filed Nov. 30, 1998, and No. 60/111,848, filed Dec. 11, 1998, all of which applications are incorporated herein by reference in their entirety.

FIELD OF THE INVENTION

This invention relates to methods of oxidizing cyclohexane to adipic acid and more specifically, how to remove catalyst as a solution after the reaction, preferably for recycling.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process," the "Boric Acid Process," and the "Direct Synthesis Process," which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase." However, no attention has been paid so far to the importance of the two phases, except for separating the adipic from the "Polar Phase" and recycling these phases to the reactor partially or totally with or without further treatment.

It is also important to note that most studies on the Direct Synthesis have been conducted in a batch mode, literally or for all practical purposes.

As aforementioned, there is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among others, may be considered as representative of oxidation processes relative to the preparation of diacids and other intermediate oxidation products.

U.S. Pat. No. 5,463,119 (Kollar) discloses a process for the oxidative preparation of C5–C8 aliphatic dibasic acids by
(1) reacting,
   (a) at least one saturated cycloaliphatic hydrocarbon having from 5 to 8 ring carbon atoms in the liquid phase and
   (b) an excess of oxygen gas or an oxygen-containing gas in the presence of
   (c) a solvent comprising an organic acid containing only primary and/or secondary hydrogen atoms and
   (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of C5–C8 aliphatic dibasic acids through oxidation of corresponding saturated cycloaliphatic hydrocarbons by
(1) reacting, at a cycloaliphatic hydrocarbon conversion level of between about 7% and about 30%,
   (a) at least one saturated cycloaliphatic hydrocarbon having from 5 to 8 ring carbon atoms in the liquid phase and
   (b) an excess of oxygen gas or an oxygen containing gas mixture in the presence of
   (c) less than 1.5 moles of a solvent per mole of cycloaliphatic hydrocarbon (a), wherein said solvent comprises an organic acid containing only primary and/or secondary hydrogen atoms and
   (d) at least about 0.002 mole per 1000 grams of reaction mixture of a polyvalent heavy metal catalyst; and
(2) isolating the C5–C8 aliphatic dibasic acid.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° C. to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Obersteiner et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

PCT International Publication WO 96/03365 (Constantini et al.) discloses a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

The patent literature is inconsistent and at least confusing regarding addition or removal of water in oxidations. For example:

U.S. Pat. No. 5,221,800 (Park et al.) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al.) discloses a process claiming improved yields by the addition of water at the beginning of the reaction, generally of the order of 0.5 to 15% relative to monobasic aliphatic acid solvent, and preferably 1 to 10% relative to the solvent.

U.S. Pat. No. 3,390,174 (Schultz et al.) discloses a process claiming improved yields of aliphatic dibasic acids when oxidizing the respective cyclic hydrocarbons at temperatures between 130° C. and 160° C., while removing the water of reaction substantially as quickly as it is formed.

None of the above references, or any other references known to the inventors disclose, suggest or imply, singly or in combination, control of oxidation reactions subject to the intricate and critical controls and requirements of the instant invention as described and claimed.

Our U.S. Pat. Nos. 5,580,531, 5,558,842, 5,502,245, and co-pending application Ser. Nos. 08/477,195 (filed Jun. 7, 1995), 08/587,967 (filed Jan. 17, 1996), and 08/620,974 (filed Mar. 25, 1996), all of which are incorporated herein by reference, describe methods and apparatuses relative to controlling reactions in atomized liquids. Co-pending U.S. application Ser. Nos. 08/812,847, filed on Mar. 6, 1997; and 08/824,992, filed on Mar. 27, 1997; are both also incorporated herein by reference.

All of the following patent applications, which were filed simultaneously on May 21, 1997, are also incorporated herein by reference:

Ser. No. 08/859,985 of Eustathios Vassiliou, Mark W. Dassel, David C. DeCoster, Ader M. Rostami, and Sharon M. Aldrich, titled "Methods and Devices for Controlling the Reaction Rate of a Hydrocarbon to an Intermediate Oxidation Product by Pressure Drop Adjustments;"

Ser. No. 08/861,281 of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Intermediate Oxidation Product by Monitoring Flow of Incoming and Outcoming Gases;"

Ser. No. 08/861,180 of David C. DeCoster, Ader M. Rostami, Mark W. Dassel, and Eustathios Vassiliou, titled "Methods and Devices for Controlling the Oxidation Rate of a Hydrocarbon by Adjusting the Ratio of the Hydrocarbon to a Rate-Modulator;"

Ser. No. 08/861,176 of Mark W. Dassel, Eustathios Vassiliou, David C. DeCoster, and Ader M. Rostami, titled "Methods of Preparing an Intermediate Oxidation Product from a Hydrocarbon by Utilizing an Activated Initiator";

Ser. No. 08/859,890 of Ader M. Rostami, Mark W. Dassel, Eustathios Vassiliou, David C. DeCoster, titled "Methods and Devices for Controlling the Oxidation of a Hydrocarbon to an Acid by Regulating Temperature/Conversion Relationship in Multi-Stage Arrangements;" and Ser. No. 08/861,210 of Eustathios Vassiliou, David C. DeCoster, Ader M. Rostami, and Mark W. Dassel, titled "Pseudo-Plug-Flow Reactor."

Further, patent application Ser. No. 08/876,692, filed on Jun. 16, 1997, of Ader M. Rostami, David C. DeCoster, Eustathios Vassiliou, Mark W. Dassel, and Sharon M. Aldrich, titled "Methods and Devices for Controlling Hydrocarbon Oxidations to Respective Acids by Adjusting the Water Level during the Reaction" is also incorporated herein by reference.

PCT patent application PCT/US97/10830, filed on Jun. 23, 1997 of Mark W. Dassel, David C. DeCoster, Ader M. Rostami, Eustathios Vassiliou, and Sharon M. Aldrich, titled "Methods and Devices for Oxidizing a Hydrocarbon to Form an Acid" is incorporated herein by reference.

Also, PCT patent application PCT/US97/12944, filed on Jun. 23, 1997, of David C. DeCoster, Eustathios Vassiliou, Mark W. Dassel, Sharon M. Aldrich, and Ader M. Rostami, titled "Methods and Devices for Controlling the Reaction Rate and/or Reactivity of Hydrocarbon to an Intermediate Oxidation Product by Adjusting the Oxidant Consumption Rate" is incorporated herein by reference.

In addition, patent application Ser. No. 08/900,323, filed on Jul. 25, 1997, of Eustathios Vassiliou, Mark W. Dassel, Sharon M. Aldrich, Ader M. Rostami, and David C. DeCoster, titled "Methods and Devices for Controlling Hydrocarbon Oxidations to Respective Acids by Adjusting the Solvent to Hydrocarbon Ratio" is also incorporated herein by reference.

SUMMARY OF THE INVENTION

As aforementioned, this invention relates to methods of oxidizing hydrocarbons, such as cyclohexane for example, to respective intermediate oxidation products, such as adipic acid for example, and more specifically, how to remove catalyst in solution after the reaction, preferably for recycling. More particularly, this invention pertains to a method of treating a reaction mixture produced by direct oxidation of cyclohexane to adipic acid, the reaction mixture comprising a monobasic acid solvent having only primary and/or secondary hydrogen atoms, water, and a catalyst, the method being characterized by steps of:

(a) removing a major part of the monobasic acid solvent;
(b) adding water and a first constituent, the first constituent being substantially non-solvent for the catalyst, in such quantities so as to form or maintain a homogeneous solids-free single liquid phase in absence of the major part of the monobasic acid solvent at a desired first temperature;
(c) extracting with water a major part of the catalyst contained in the homogeneous solids-free single liquid phase, thus forming a solids-free aqueous liquid phase containing the major part of the catalyst, and a solids-free non-aqueous liquid phase; and
(d) separating the solids-free aqueous liquid phase from the solids-free non-aqueous liquid phase;

wherein steps (a) and (b) are not necessarily sequential.

This invention also relates to a method of treating a reaction mixture produced by direct oxidation of cyclohexane to adipic acid, the reaction mixture comprising a monobasic acid solvent having only primary and/or secondary hydrogen atoms, water, and a catalyst, the method being characterized by steps of:

(a) removing a major part of the monobasic acid solvent;
(b) adding water and a first constituent, the first constituent being substantially non-solvent for the catalyst, in such quantities so as to form or maintain a homogeneous solids-free single liquid phase in absence of the major part of the monobasic acid solvent at a desired first temperature;
(c) adding an adequate amount of a second constituent to form a solids-free aqueous polar phase containing dissolved catalyst and a solids-free non-aqueous phase, the second constituent being a substantially non-solvent for the catalyst and a substantially non-solvent for dibasic acids; and
(d) separating the solids-free aqueous liquid phase from the solids-free non-aqueous liquid phase;

wherein steps (a) and (b) are not necessarily sequential.

In either method or equivalent methods, is important that steps (a), (b), (c), and (d) precede any major removal of adipic acid from the reaction mixture in order to maintain a single solids-free liquid phase in a rather large region and improve solubility of catalyst in a mixture containing the first constituent, as it will be explained later in more detail. It is also important that the first constituent is a good solvent for dibasic acids.

The method may further comprise a step of recycling the solids-free aqueous liquid phase to a reaction zone, in which reaction zone the cyclohexane is oxidized to adipic acid, either directly or indirectly, and/or with or without removal of water, and/or with or without addition of monobasic acid solvent, followed by a step of removing a major part of the adipic acid contained in the solids-free non-aqueous liquid phase. The method may also comprise a step of removing dibasic acids by extracting with water from the solids-free non-aqueous liquid phase before or after concentrating said solids-free non-aqueous liquid phase, or by lowering the temperature, or by adding second constituent, or by a combination of the above.

The step of removing the major part of the adipic acid is preferably conducted by a method selected from a group consisting of concentrating the solids-free non-aqueous liquid phase, extracting with water, lowering the temperature, adding second constituent, and a combination thereof. The step of concentrating the solids-free non-aqueous liquid phase preferably comprises a step of removing at least partially the first constituent at a second temperature higher than the first temperature, and/or under vacuum.

Miscellaneous esters, which were produced as byproducts in the reaction chamber, and contained in the solids-free non-aqueous liquid phase, are preferably hydrolyzed.

The method is particularly applicable in the case that the monobasic acid solvent comprises acetic acid, the first constituent comprises cyclohexanone, the second constituent comprises cyclohexane, and the catalyst comprises a cobalt compound.

The methods of the invention may further comprise a step of reacting the adipic acid with a reactant selected from a group consisting of a polyol, a polyamine, and a polyamide in a manner to form a polymer of a polyester, or a polyamide, or a (polyimide and/or polyamideimide), respectively. In addition, the method may also comprise a step of spinning the polymer into fibers, and/or adding to the polymer, fillers and/or other additives to form composites.

Cooling at one or more stages may be performed preferably by condensation or other cooling means, such as cooling coils for example, or both.

BRIEF DESCRIPTION OF THE DRAWINGS

The reader's understanding of this invention will be enhanced by reference to the following detailed description taken in combination with the drawing figures, wherein.

DETAILED DESCRIPTION OF THE INVENTION

As aforementioned, this invention relates to methods and devices for oxidizing cyclohexane to adipic acid for example, and more specifically, how to remove catalyst in solution after the reaction, preferably for recycling.

Proper catalyst handling in oxidation reactions has always been a considerable problem in the art. According to the present invention, the catalyst is separated in a liquid form dissolved in an aqueous phase, and preferably returned to the reaction chamber with or without any further treatment.

It was found by the inventors that the reaction mixture after oxidation of the cyclohexane to adipic acid to a desired degree of conversion, and after removal of the remaining cyclohexane along with the majority of the monobasic acid solvent, such as acetic acid for example, may attain or be maintained in a solids-free, monophasic liquid state after addition of a non-solvent for the catalyst (first constituent), and water within a wide range, especially when a large amount of adipic acid is present. The catalyst may then be extracted with an additional amount of water, or by a temperature decrease, or by addition of second constituent, and preferably returned to the reaction chamber with or without any further treatment.

For better clarification of this invention, the examples given below assume that the reaction mixture contains a solvent comprising acetic acid, the catalyst comprises a cobalt compound, the first constituent comprises cyclohexanone, and the second constituent comprises cyclohexane. It should be understood, however, that the teachings of this invention are applicable to different solvents, constituents, solvents, and catalysts than the ones used in the examples. Only minor modifications may be needed to fit each individual case.

The first constituent, which is substantially non-solvent for the catalyst, but preferably a solvent for dibasic acids and esters, is preferably a compound which has a polarity in the range of polarities exhibited by alcohols, and ketones. The second constituent which is substantially non-solvent for the catalyst and substantially non-solvent for the dibasic acids is preferably a compound having a polarity in the range of polarities exhibited by hydrocarbons.

"Major" and "majority" regarding a moiety mean more than 50% of said moiety by weight.

Figure 1:
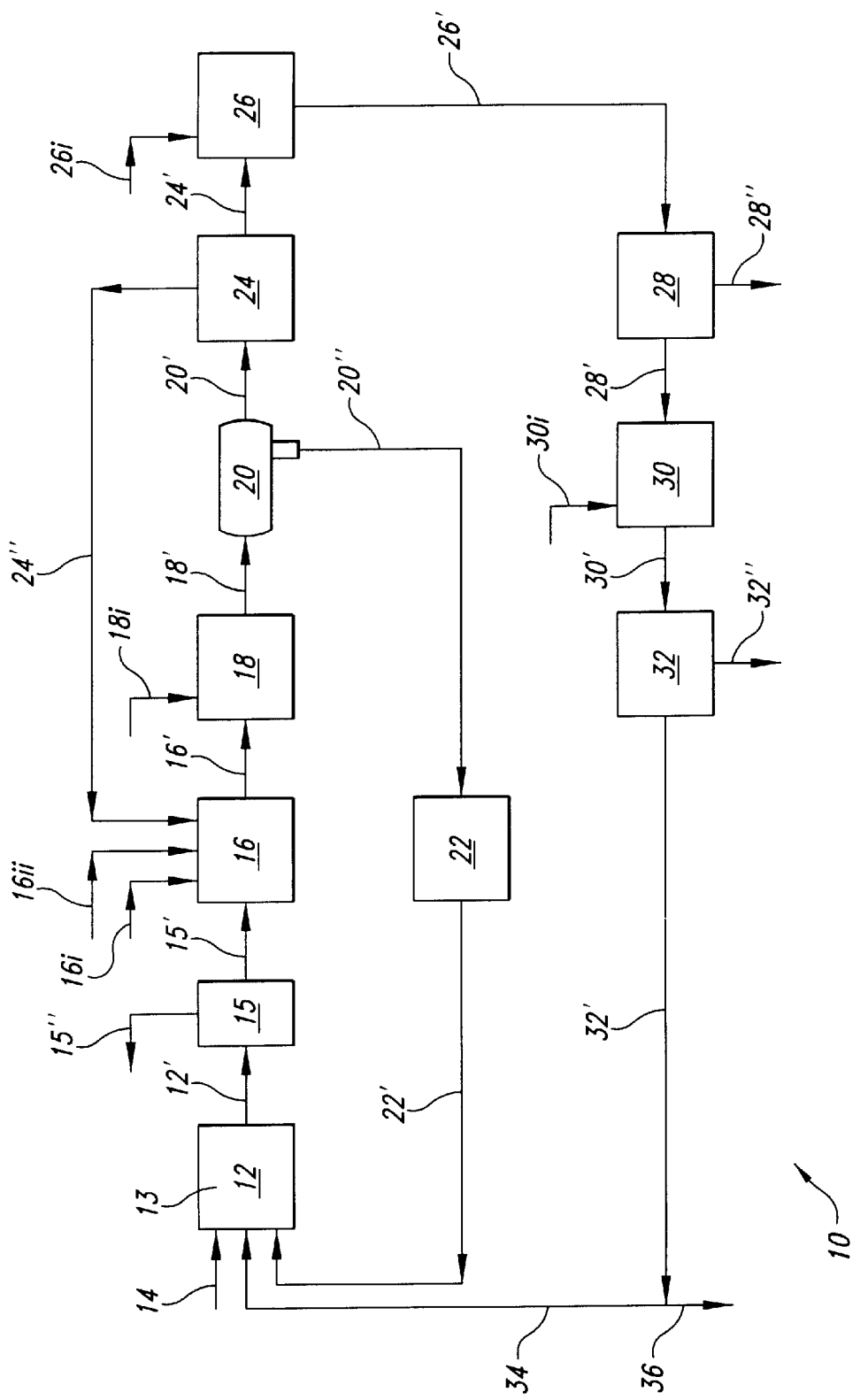
FIG. 1 illustrates a block diagram of a preferred embodiment of the present invention.

Referring now to FIG. 1, there is depicted a reactor system 10 comprising a reaction chamber 12 connected to a feeding line 14. The feeding line 14 is shown as a single line for purposes of brevity and simplicity, but it represents all feeding lines for introducing reactants and other matter to the reaction chamber 12. The feeding lines represented by 14 may include, if appropriate, devices such as for example mixing vessels, heaters, coolers, etc.

The reaction chamber 12 is a reaction chamber suitable for oxidizing cyclohexane to adipic acid in a direct synthesis. Such reaction chambers have been disclosed in a number of our patents and patent applications, as well as in the relevant art. The reaction chamber 12 encloses a reaction zone 13. Miscellaneous devices utilized in many cases along with a reaction chamber of this sort, are not shown in FIG. 1 for purposes of clarity and brevity. Such devices include, but are not limited to condensers, decanters, etc.

The reaction chamber 12 is connected to a first evaporator or still 15 through line 12', which in turn is connected to distillate line 15" and to a first mixing tank 16 through line 15'. The mixing tank 16 may be a heated and/or cooled tank, if so desired. The mixing tank 16 is connected to feeding lines 16i and 16ii and, through line 16', to a second mixing tank. The second mixing tank 18 may be a heated and/or cooled tank, if so desired. The second mixing tank 18 is in turn connected to a feeding line 18i, and to a first decanter 20 through line 18'. The first decanter 20 is connected to an optional catalyst treatment station 22 through line 20" and to a first concentration chamber 24 through line 20'. The optional catalyst treatment station 22 is connected to the reaction chamber 12 through line 22'. The first concentration chamber 24 is connected to the first mixing tank 16 through line 24", and to a first precipitation chamber 26 through line 24'. The first precipitation chamber 26 is connected to an optional feeding line 26i and to a first solids removal chamber 28 through line 26'. The solids removal chamber 28 is connected to line 28" (used for removal of solids), and to a hydrolysis chamber 30 through line 28'. The hydrolysis chamber 30 is connected to an optional line 30i and to a second solids removal chamber 32 through line 30'. The second solids removal chamber 32 is in turn connected to line 32" through which solids are removed and line 32', which line 32' is split into recycle line 34 and to a further treatment line 36.

Miscellaneous devices which may be attached to the reaction chamber 12 or any other chamber are not shown in FIG. 1 for purposes of brevity and clarity.

In operation of this embodiment, raw materials and other matter required for the oxidation of cyclohexane to adipic acid enter the reaction chamber 12 through feeding line 14. Feeding line 14 represents more than 1 line through which the feeding occurs, but it is shown as a single line for purposes of clarity and brevity. In an example of the direct oxidation of cyclohexane to adipic acid, the cyclohexane is oxidized by oxygen in the presence of a monobasic acid solvent, such as acetic acid for example, a catalyst, such as a cobalt compound for example, and an optional initiator, such as cyclohexanone or acetaldehyde for example. The reaction mixture enters the first evaporator or still 15 in which substantially all the cyclohexane and the major part of the monobasic acid, acetic acid for example, are removed through the distillate line 15". The distillate line 15" may lead to a condenser (not shown) and a decanter (not shown).

It is preferable that the removal of the cyclohexane and the monobasic acid solvent by distillation takes place under vacuum and at a temperature lower than 100° C.

The residual mixture produced in this manner is lead to the first mixing tank 16 through line 15'. A non-solvent for catalyst, and preferably solvent for dibasic acids (first constituent), such as cyclohexanone for example, is added to the mixing tank 16 through line 16ii and through line 24", while water enters the mixing tank 16 through feeding line 16i.

It is important to note that the first evaporator 15 and the mixing tank 16 preferably constitute a single vessel in most occasions. They are shown in FIG. 1 as two separate vessels in order to stress the steps of the operation. In this mode the addition of first constituent takes place in the same vessel in which the monobasic acid solvent is being removed by distillation.

It was unexpectedly found by the inventors that there is a wide range within which the system (residual mixture)/(first constituent)/(water) remains in a solids-free single liquid phase. It is preferable that the (residual mixture)/(first constituent) ratio is in the range of 1/1 to 1/5 with an adequate amount of water to maintain the solution solids-free, but not more than an amount which causes formation of a second liquid phase. It was also found by the inventors that this range is extraordinarily wider in the case that at least most of the adipic acid produced in the reactor is still present, and not removed in previous steps.

From the first mixing tank, the homogeneous solids-free monophasic liquid is transferred to the second mixing tank 18 through line 16'. Water is added to the second mixing tank 18 through line 18i. The amount of water added is adequate to produce two liquid phases; a solids-free aqueous liquid phase containing at least the major part of the catalyst, and a solids-free non-aqueous liquid phase. Production of said two liquid phases may be achieved by lowering the temperature, or by adding second constituent, or a combination of the three.

The two solids-free liquid phases are separated in the first decanter 20, to which they are transferred from the second mixing tank 18 through line 18'. The solids-free aqueous liquid phase containing at least the major part of the catalyst is preferably recycled to the reaction chamber 12, either directly (untreated) or indirectly through the catalyst treatment station 22. The treatment may be as simple as removing part of the water and/or adding some monobasic acid solvent, such as acetic acid for example.

The solids-free non-aqueous liquid phase is transferred to the first concentration chamber 24, wherein at least the majority of the first constituent, cyclohexanone for example, is removed by distillation or other techniques, and it is recycled to the first mixing tank 16 through line 24". Thus, only complementary amounts of first constituent have to be added to the first mixing tank 16 through line 16ii.

The concentrated mixture is transferred to the first precipitation chamber 26, where adipic acid is precipitated, preferably after cooling and/or after addition of water through line 26i. The first precipitation chamber 26 may also represent an extractor for extracting the adipic acid and other moieties with hot water from the rest of the concentrated mixture, and a crystallizer for precipitating the adipic acid in the form of crystals. Adipic acid may also be precipitated by introduction of second constituent.

The major part of the adipic acid is removed in a first solids removal chamber 28 through line 28", and the remainder is transferred to the hydrolysis chamber 30, in which more water is preferably added trough line 30i. Hydrolysis takes place in the hydrolysis chamber by any technique well known to the art. Examples are hydrothermal hydrolysis (hydrolysis conducted at elevated temperatures and pressures), acidic hydrolysis by addition of a strong acid, preferably by using a resin with strong acid pending groups, such as Nafion® for example, basic hydrolysis by addition of a strong base, etc.

After hydrolysis, a crystallization of adipic acid is conducted, and the adipic acid removed in the second solids removal chamber 32 through line 32". The remainder follows line 32", and it may split into line 34 for recycling to the reaction chamber 12, and into line 36 for further treatment or disposal.

Figure 2:
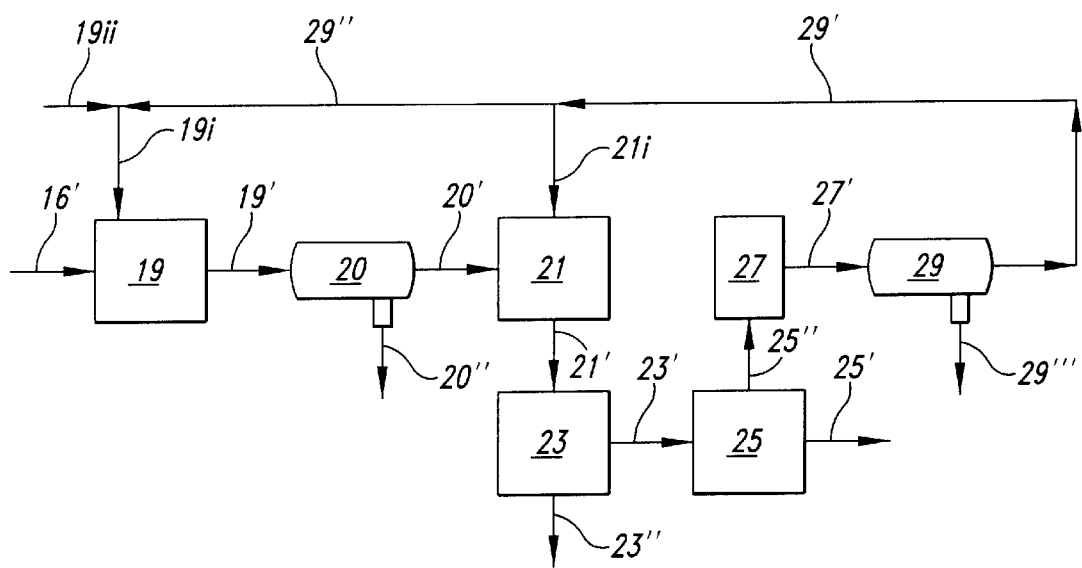
FIG. 2 illustrates a block diagram of another preferred embodiment of the present invention.

According to another embodiment of the instant invention, the second mixing tank 18 and the first decanter 20 have been replaced by the arrangement illustrated in FIG. 2.

The first mixing tank 16 (see FIG. 1) is connected to a third mixing tank 19 through line 16'. The third mixing tank 19 is connected to the first decanter 20 through line 19', which in turn is connected to a second precipitation chamber 21 through line 20'. In turn, the second precipitation chamber 21 is connected to a third solids removal chamber 23 through line 21'. The third solids removal chamber 23 is connected to a second evaporator 25 through line 23'. The second evaporator 25 is connected to the first concentration chamber 24 (see FIG. 1) through line 25'. The second evaporator 25 is also connected to a condenser 27 through line 25", which in turn is connected to a second decanter 29. The second decanter 29 is connected to the third mixing tank 19 through the sequence of lines 29', 29", and 19i, and to the second precipitation chamber 21 through the sequence of lines 29' and 21i.

In operation of this embodiment, the solids-free, monophasic liquid form the first mixing tank 16 (see FIG. 1) is transferred to the third mixing tank 19, wherein an adequate amount of second constituent is added through line 19i. It is preferable that most of the second constituent is provided by the second decanter 29, as will be discussed later. Additional second constituent may be added through line 19ii. Rather small amounts of second constituent are needed in this step to form two solids-free liquid phases; a solids-free polar phase and a solids-free non-polar phase. Attention has to be paid in avoiding excessive addition of second constituent, which causes precipitation of adipic acid. The solids-free polar phase contains mainly water with dissolved catalyst. This polar phase, containing the dissolved catalyst, is removed through line 20", and is preferably recycled to the reaction chamber 12 (see FIG. 1) either directly or indirectly through the catalyst treatment station 22 (see FIG. 1), wherein operations such as removal of water, or addition of acid, or both, for example, may be performed before recycling to the reaction chamber 12 (see FIG. 1).

The solids-free non-polar phase is transferred to the second precipitation chamber 21, wherein additional second constituent is added in an adequate amount to cause precipitation of adipic acid. Temperature decrease may also be used for this purpose, either by itself or in combination with water addition, or in combination with other parameters having the tendency to precipitate the adipic acid. The precipitated adipic acid is separated from the liquid phase in the third solids removal chamber 23, and removed through line 23". Filtration or centrifugation are preferable methods of solids separation. The remaining liquid phase, after the separation of adipic acid, is transferred through line 23' to the evaporator 25, wherein second constituent and water are evaporated, condensed in condenser 27, and separated in the second decanter 29. The water is removed through line 29", while the second constituent is preferably recycled to the third mixing tank 19 through the sequence of lines 29', 29", and 19i, and to the second precipitation chamber 21 through the sequence of lines 29' and 21i. The liquid remaining after removal of second constituent and water is transferred to the first concentration chamber 4 (see FIG. 1) for further treatment as described in the previous embodiment.

It should be understood that according to the present invention, any liquids or gases or off-gases may be recycled totally or partially from any section to any other section, if so desired. Further, any combinations of the exemplifying embodiments, in part or in total, or any equivalent arrangements or any combinations of equivalent arrangements may be utilized, and are within the scope of the present invention.

Although miscellaneous functions are preferably controlled by a computerized controller, it is possible, according to this invention, to utilize any other type of controller or even manual controls and/or labor for controlling one or more functions. Preferred computerized controllers are artificially intelligent systems (expert systems, neural networks, and fuzzy logic systems, well known to the art). Of the three types of the artificially intelligent systems, the neural network, which is a learning system, collects information from different places of the device (for example pressure, temperature, chemical or other analysis, etc.), stores this information along with the result (pressure drop rate, reaction rate, reactivity, and the like, for example), and is programmed to use this information in the future, along with other data if applicable, to make decisions regarding the action to be taken at each instance. The expert systems are programmed based on the expertise of experienced human beings. The fuzzy logic systems are based on intuition rules in addition to expertise rules.

Oxidations according to this invention, are non-destructive oxidations, wherein the oxidation product is different than carbon monoxide, carbon dioxide, and a mixture thereof, such as adipic acid for example. Of course, small amounts of these compounds may be formed along with the oxidation product, which may be one product or a mixture of products.

Regarding adipic acid, the preparation of which is especially suited to the methods of this invention, general information may be found in a plethora of U.S. Patents, among other references. These include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Diacids or other suitable compounds may be reacted, according to well known techniques to the art, with a reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers. Furthermore, additives may be combined with the polymers and/or fibers, where fillers are one type of additive, to thereby form a composite. Thus, the methods of the present invention may include a step of polymerizing the adipic acid of this process as described above to form polymers and fibers, as well as adding to the polymer (or fiber) fillers and/or other additives to form composites, and a combination thereof.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

What is claimed is:

1. A method of treating a reaction mixture produced by direct oxidation of cyclohexane to adipic acid, the reaction mixture comprising a monobasic acid solvent having only primary and/or secondary hydrogen atoms, water, and a catalyst, the method being characterized by steps of:
   (a) removing a major part of the monobasic acid solvent;
   (b) adding water and a first constituent, the first constituent being substantially non-solvent for the catalyst, in such quantities so as to form or maintain a homogeneous solids-free single liquid phase in absence of the major part of the monobasic acid solvent at a desired first temperature;
   (c) extracting with water a major part of the catalyst contained in the homogeneous solids-free single liquid phase, thus forming a solids-free aqueous liquid phase containing the major part of the catalyst, and a solids-free non-aqueous liquid phase; and
   (d) separating the solids-free aqueous liquid phase from the solids-free non-aqueous liquid phase;
   wherein steps (a) and (b) are not necessarily sequential.

2. A method as defined in claim 1 wherein steps (a), (b), (c), and (d) precede any major removal of adipic acid from the reaction mixture.

3. A method as defined in claim 1, further comprising a step of recycling the solids-free aqueous liquid phase to a reaction zone, in which reaction zone the cyclohexane is oxidized to adipic acid, either directly or indirectly, and/or with or without removal of water, and/or with or without addition of monobasic acid solvent.

4. A method as defined in claim 1, further comprising a step of removing a major part of the adipic acid contained in the solids-free non-aqueous liquid phase.

5. A method as defined in claim 4 wherein the step of removing the major part of the adipic acid comprises steps selected from a group consisting of concentrating the solids-free non-aqueous liquid phase, extracting with water, lowering temperature, adding second constituent, and a combination thereof.

6. A method as defined in claim 5 wherein the step of concentrating the solids-free non-aqueous liquid phase comprises a step of removing at least partially the first constituent by decreasing the first temperature, and/or by applying vacuum.

7. A method as defined in claim 5, further comprising a step of hydrolyzing esters contained in the solids-free non-aqueous liquid phase.

8. A method as defined in claim 6, further comprising a step of extracting dibasic acids with water from the solids-free non-aqueous liquid phase before or after concentrating said solids-free non-aqueous liquid phase.

9. A method as defined in claim 1 wherein the monobasic acid solvent comprises acetic acid, the first constituent comprises cyclohexanone, and the catalyst comprises a cobalt compound.

10. A method as defined in claim 2 wherein the monobasic acid solvent comprises acetic acid, the first constituent comprises cyclohexanone, and the catalyst comprises a cobalt compound.

11. A method as defined in claim 3 wherein the monobasic acid solvent comprises acetic acid, the first constituent comprises cyclohexanone, and the catalyst comprises a cobalt compound.

12. A method as defined in claim 4 wherein the monobasic acid solvent comprises acetic acid, the first constituent comprises cyclohexanone, and the catalyst comprises a cobalt compound.

13. A method as defined in claim 8 wherein the monobasic acid solvent comprises acetic acid, the first constituent comprises cyclohexanone, and the catalyst comprises a cobalt compound.

14. A method as defined in claim 1, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

15. A method as defined in claim 14, further comprising a step selected from a group consisting of spinning the polymer into fibers, adding to the polymer fillers and/or other additives to form composites, and a combination thereof.

16. A method as defined in claim 2, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

17. A method as defined in claim 16, further comprising a step selected from a group consisting of spinning the polymer into fibers, adding to the polymer fillers and/or other additives to form composites, and a combination thereof.

18. A method as defined in claim 3, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

19. A method as defined in claim 18, further comprising a step selected from a group consisting of spinning the polymer into fibers, adding to the polymer fillers and/or other additives to form composites, and a combination thereof.

20. A method as defined in claim 9, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

21. A method as defined in claim 20, further comprising a step selected from a group consisting of spinning the polymer into fibers, adding to the polymer fillers and/or other additives to form composites, and a combination thereof.

22. A method of treating a reaction mixture produced by direct oxidation of cyclohexane to adipic acid, the reaction mixture comprising a monobasic acid solvent having only primary and/or secondary hydrogen atoms, water, and a catalyst, the method being characterized by steps of:

(a) removing a major part of the monobasic acid solvent;

(b) adding water and a first constituent, the first constituent being substantially non-solvent for the catalyst, in such quantities so as to form or maintain a homogeneous solids-free single liquid phase in absence of the major part of the monobasic acid solvent at a desired first temperature;

(c) adding an adequate amount of a second constituent to form a solids-free aqueous polar phase containing dissolved catalyst and a solids-free non-aqueous phase, the second constituent being a substantially non-solvent for the catalyst and a substantially non-solvent for dibasic acids; and (d) separating the solids-free aqueous liquid phase from the solids-free non-aqueous liquid phase;

wherein steps (a) and (b) are not necessarily sequential.

23. A method as defined in claim 22 wherein steps (a), (b), (c), and (d) precede any major removal of adipic acid from the reaction mixture.

24. A method as defined in claim 23, further comprising a step of removing adipic acid by introducing additional cyclohexane in an adequate amount to precipitate adipic acid, and/or by decreasing temperature.

25. A method as defined in claim 22, further comprising a step of concentrating the solids-free non-aqueous liquid phase and a step of removing at least partially the first constituent at a second temperature higher than the first temperature, and/or by applying vacuum.

26. A method as defined in claim 23, further comprising a step of concentrating the solids-free non-aqueous liquid phase and a step of removing at least partially the first constituent at a second temperature higher than the first temperature, and/or by applying vacuum.

27. A method as defined in claim 24, further comprising a step of concentrating the solids-free non-aqueous liquid phase and a step of removing at least partially the first constituent at a second temperature higher than the first temperature, and/or by applying vacuum.

28. A method as defined in claim 23, further comprising a step of recycling the solids-free aqueous liquid phase to a reaction zone, in which reaction zone the cyclohexane is oxidized to adipic acid, either directly or indirectly, and/or with or without removal of water, and/or with or without addition of monobasic acid solvent.

29. A method as defined in claim 22 wherein the monobasic acid solvent comprises acetic acid, the first constituent comprises cyclohexanone, the second constituent comprises cyclohexane, and the catalyst comprises a cobalt compound.

30. A method as defined in claim 23 wherein the monobasic acid solvent comprises acetic acid, the first constituent comprises cyclohexanone, the second constituent comprises cyclohexane, and the catalyst comprises a cobalt compound.

31. A method as defined in claim 24 wherein the monobasic acid solvent comprises acetic acid, the first constituent comprises cyclohexanone, the second constituent comprises cyclohexane, and the catalyst comprises a cobalt compound.

32. A method as defined in claim 22, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

33. A method as defined in claim 32, further comprising a step selected from a group consisting of spinning the polymer into fibers, adding to the polymer fillers and/or other additives to form composites, and a combination thereof.

34. A method as defined in claim 23, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

35. A method as defined in claim 34, further comprising a step selected from a group consisting of spinning the polymer into fibers, adding to the polymer fillers and/or other additives to form composites, and a combination thereof.

36. A method as defined in claim 24, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

37. A method as defined in claim 36, further comprising a step selected from a group consisting of spinning the polymer into fibers, adding to the polymer fillers and/or other additives to form composites, and a combination thereof.

38. A method as defined in claim 25, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

39. A method as defined in claim 38, further comprising a step selected from a group consisting of spinning the polymer into fibers, adding to the polymer fillers and/or other additives to form composites, and a combination thereof.

40. A method as defined in claim 26, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

41. A method as defined in claim 40, further comprising a step selected from a group consisting of spinning the polymer into fibers, adding to the polymer fillers and/or other additives to form composites, and a combination thereof.

42. A method as defined in claim 27, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

43. A method as defined in claim 42, further comprising a step selected from a group consisting of spinning the polymer into fibers, adding to the polymer fillers and/or other additives to form composites, and a combination thereof.

44. A method as defined in claim 28, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

45. A method as defined in claim 44, further comprising a step selected from a group consisting of spinning the polymer into fibers, adding to the polymer fillers and/or other additives to form composites, and a combination thereof.

46. A method as defined in claim 29, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

47. A method as defined in claim 46, further comprising a step selected from a group consisting of spinning the polymer into fibers, adding to the polymer fillers and/or other additives to form composites, and a combination thereof.

48. A method as defined in claim 30, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

49. A method as defined in claim 48, further comprising a step selected from a group consisting of spinning the polymer into fibers, adding to the polymer fillers and/or other additives to form composites, and a combination thereof.

50. A method as defined in claim 31, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

51. A method as defined in claim 50, further comprising a step selected from a group consisting of spinning the polymer into fibers, adding to the polymer fillers and/or other additives to form composites, and a combination thereof.

* * * * *